United States Patent [19]

Hutchins et al.

[11] 4,281,687
[45] Aug. 4, 1981

[54] FLUID STORAGE DEVICE

[75] Inventors: Burleigh M. Hutchins, North Attleboro; Louis Abrahams, Worcester, both of Mass.

[73] Assignee: Waters Associates, Inc., Milford, Mass.

[21] Appl. No.: 124,309

[22] Filed: Feb. 25, 1980

Related U.S. Application Data

[63] Continuation of Ser. No. 10,686, Feb. 9, 1979, Pat. No. 4,245,963.

[51] Int. Cl.³ .............................................. E03B 7/10
[52] U.S. Cl. .................................................. 138/28
[58] Field of Search ............................. 138/26, 28, 30

[56] References Cited

U.S. PATENT DOCUMENTS

| | | | |
|---|---|---|---|
| 1,958,009 | 5/1934 | McKee | 138/30 |
| 3,329,093 | 7/1967 | Bear | 138/26 |
| 3,348,578 | 10/1967 | Mercer | 138/30 |
| 3,855,129 | 12/1974 | Abrahams et al. | 210/198 C |

OTHER PUBLICATIONS

*Model 6000A Solvent Delivery System*, Waters Associates, Inc., Pamphlett Published 5/78.

*Primary Examiner*—Steven L. Stephan

[57] ABSTRACT

A pump for precise, smooth delivery of liquid, particularly in liquid chromatography systems, featuring two liquid displacement elements mounted for reciprocating movement in chambers connected in series with two check valves, one displacement element serving to accumulate some of the liquid delivered by the first element and to deliver the accumulated liquid while the first element is refilling. Also disclosed is a fluid storage device for smoothing pulses from the pump comprising a flattened tube wound into a helix and placed within an annulus formed by an inner and an outer cylindrical wall. These cylindrical walls maintain the flattened tubing from expanding beyond its elastic strain limit.

2 Claims, 4 Drawing Figures

U.S. Patent  Aug. 4, 1981  4,281,687
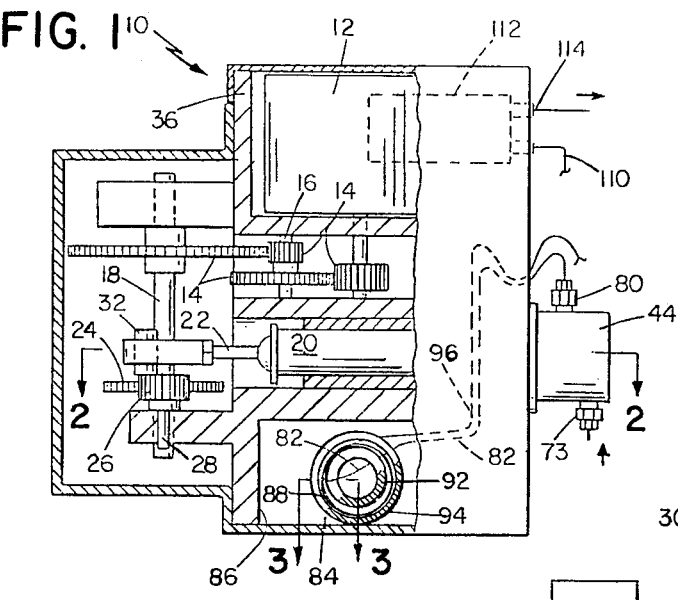
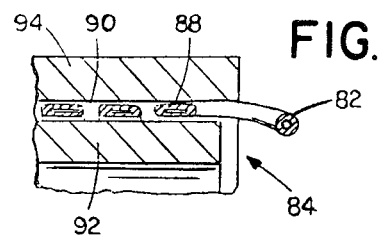
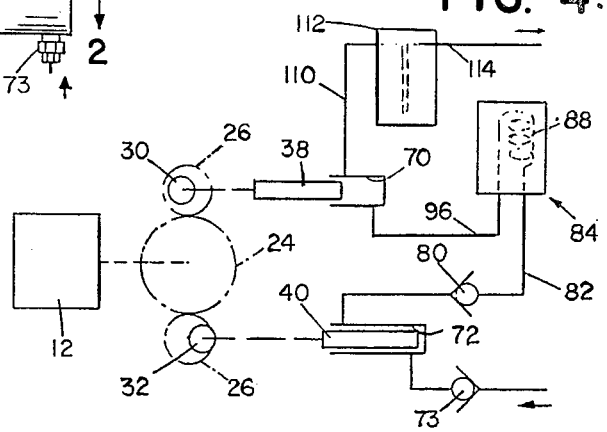
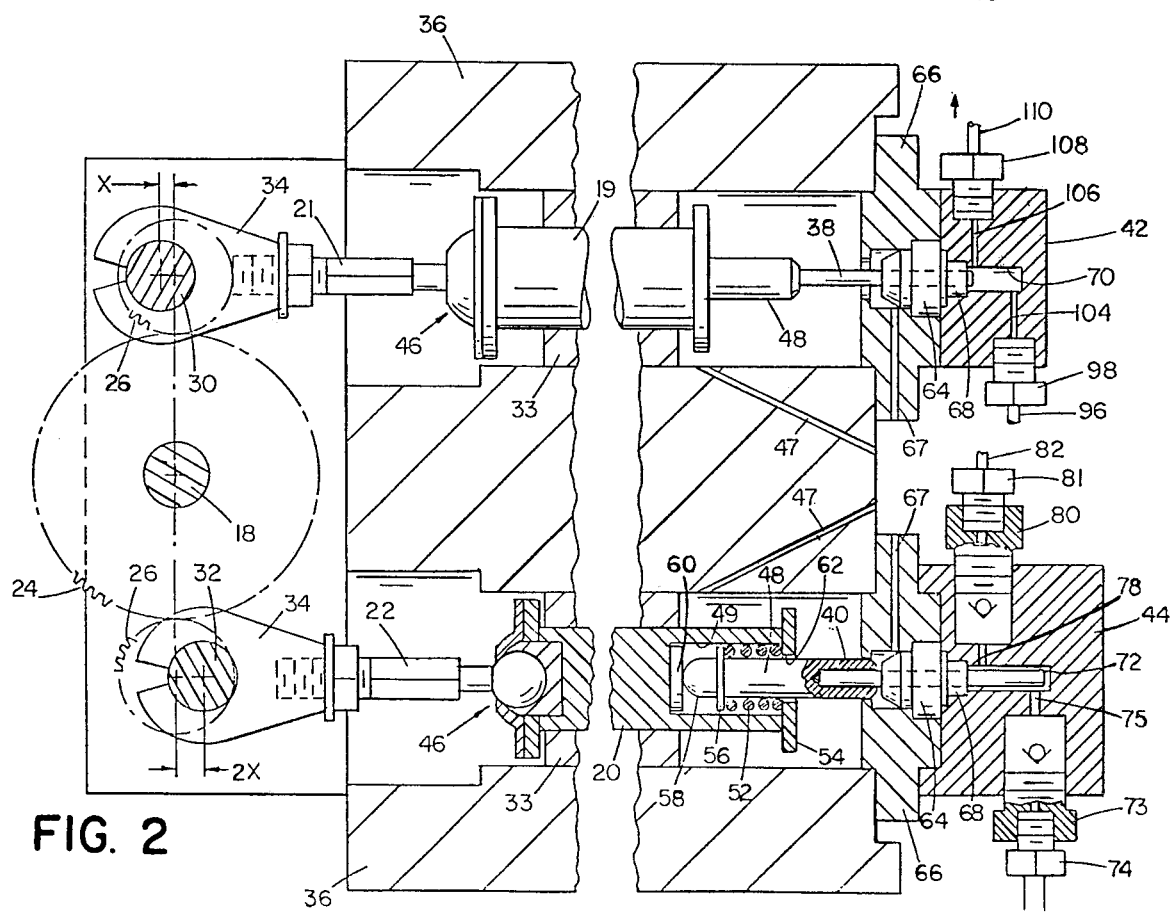

FLUID STORAGE DEVICE

This is a continuation of application Ser. No. 10,686, filed Feb. 9, 1979 now U.S. Pat. No. 4,245,963.

FIELD OF THE INVENTION

This invention relates to pumps, particularly those for delivering a smooth flow of liquid in chromatography systems.

BACKGROUND OF THE INVENTION

In chromatography and other applications, a precisely-controlled continuous flow of liquid is often desirable. Positive displacement pumps offer the desired precision, but a single piston or other displacement element can only deliver liquid during a portion of its operating cycle and must fill with incoming fluid during the remainder of the cycle. To provide a continuous output, it is conventional to use two pistons and cylinders connected in parallel, with each one delivering liquid during half of the cycle. E.g., Abrahams et al. U.S. Pat. No. 3,855,129 and Swarthout U.S. Pat. No. 3,025,803. These pumps are relatively complicated. Four check valves are generally required: one at the inlet to each cylinder and one at each outlet. And because flow through the pump is necessarily divided upstream of and then joined downstream of the two cylinders, flow mixing can result between serial flow segments entering the pump. Further, in high pressure pumps employing two such cylinders, an air bubble entering one cylinder can remain trapped there, effectively shutting down that piston and cylinder. This occurs because the other piston maintains pressure in the outlet line and thereby keeps the outlet check valve on the first cylinder closed. The first cylinder cannot generate enough pressure, because of the bubble, to open the check valve. For this reason, such pumps require careful initial bleeding and continuous monitoring thereafter. Another pump that delivers a relatively continuous flow is the very old and well known design for a hand water pump, in which water is delivered on both up and down strokes of the pump handle. There, a single piston with a step down in cross section moves through two adjacent volumes of water. Water stored in the upper volume during the down stroke is expelled on the up stroke.

As a further step towards providing continuous, smooth flow delivery in a two-cylinder pump, it is known to provide a pulse dampener downstream of or between the cylinders. Liquid stored in the dampener during high flow (and high pressure) periods of a cycle is released during transitions between cylinders when flow displaced from the cylinders is momentarily low. A length of flattened tubing that expands in cross section at high pressures is typically used for liquid storage to reduce mixing between serial flow segments. To store the flattened tubing compactly, it is conventional to bend it into many convolutions and store it inside a can filled with potting material (e.g., Waters Associates, Inc. Model 6000A pump). The tubing has also been bent into a helix and stored inside a cylindrical can.

SUMMARY OF THE INVENTION

We have discovered an improved pump for precise, smooth delivery of liquid, one particularly suited for continuous pumping of solvent in liquid chromatography. It delivers nearly as uniform and precise a flow as the pump described in Abrahams et al. U.S. Pat. No. 3,855,129 (now Waters Associates, Inc. Model 6000A), but is simpler, more reliable, and less costly. The new pump is particularly well suited for dedicated uses in which less versatility is required and slightly less precision is tolerable, such as production control in the pharmaceutical industry.

Our invention features two liquid displacement elements (e.g., plungers) mounted for reciprocating movement in two respective chambers (e.g., bores in separate heads) connected is series. Two check valves are provided, one at the inlet to the first chamber and the other in the flow path between the chambers. The displacement elements are sized and driven such that, during half of a cycle, the first element displaces liquid into the second chamber while the second element is retracting. The size and stroke of the second element are selected such that some (preferably 50 percent) of the liquid accumulates in the second chamber while the remainder is delivered through its outlet to the load. During the other half of the cycle, the accumulated liquid is delivered by the advancing second element, and the first chamber is filled by the retracting first element.

In preferred embodiments, a liquid storage device consisting of a flattened length of coiled tubing is placed in the flow path between the two chambers to deliver flow during the low flow periods when the displacement elements reverse direction, thereby smoothing flow delivery; the chambers are formed by bores slightly larger in diameter than rod-shaped plungers forming the displacement elements, and each inlet and outlet communicate with each bore at axially spaced apart locations, whereby full flushing of liquid from the chambers is achieved and little flow mixing occurs because the first fluid into the chamber is the first fluid out; the greater displacement of the first chamber is effected by drive means that makes the second plunger translate less than the first; and a stepping motor, gear drive, and push rods are used to reciprocate the plungers.

In addition to its simplicity and reliability (e.g., fewer check valves), the invention has the further advantages of being self priming (bubbles not being trapped in one chamber as with prior chromatography pumps) and causing less flow mixing (the flow being serial rather than divided).

In another aspect, our invention features a fluid storage device for smoothing fluid delivery (e.g., of a pump). The fluid storage device includes a length of flattened tubing with first and second opposed wall portions adapted to bow outward when internal pressure increases, to thereby increase the internal volume per unit length of the tubing. First and second restraining walls on either side of the tubing restrain expansion of the tubing to within the tubing's elastic strain limit, thereby allowing the tubing to expand under an increase in internal fluid pressure and to contract back to its original shape on a decrease in pressure.

In preferred embodiments, the flattened tubing is coiled in a helix and restrained within an annulus formed by inner and outer cylindrical walls.

Our fluid storage device is particularly suited for use in chromatography as a pulse dampener to smooth liquid delivery from a pump. It has the advantage of maintaining its original small volume after repeated pressure cycles because expansion is kept restrained to within the tubing's elastic strain limit. We have observed that in conventional storage devices with flattened tubing the tubing expands beyond its elastic strain limit on first use, thereby greatly enlarging the internal volume and increasing flow mixing between serial flow segments passing through the device. Such serial flow mixing can degrade chromatographic separation.

PREFERRED EMBODIMENT

We turn now to description of the structure and operation of a preferred embodiment of the invention, after first briefly describing the drawings.

Drawings

FIG. 1 is an elevation, partially cross-sectional, view of said preferred embodiment.

FIG. 2 is a cross-sectional view, shortened by cutting away a center portion, at 2—2 of FIG. 1.

FIG. 3 is a cross-sectional view at 3—3 of FIG. 1, showing a small portion of the pulse dampener of said embodiment FIG. 4 is a schematic view of the fluid circuit of said embodiment.

STRUCTURE

Referring to FIG. 1, there is shown solvent delivery pump 10. It has a drive mechanism consisting of synchonous stepping motor 12 (Superior Electric Slo-Syn MO91-FD09), gears 14 and intermediate shaft 16 for rotating main shaft 18. Turning to FIG. 2, it can be seen that rotation of shaft 18 reciprocates crank arms 21, 22 via main gear 24 and smaller gears 26 rotating on independent shafts 28. Plastic end fittings 34 attach crank arms 21, 22 to radially-offset journals 30, 32. Journal 30 is offset distance $\times$ ($\frac{1}{8}$ inch) from the axis of shaft 28, and journal 32 twice that distance, or $2 \times$ ($\frac{1}{8}$ inch). Ball-joint fastener 46 connects crank arms 21, 22 to push rods 19, 20. The ball-joint allows the crank arms to follow lateral movement of journals 30, 32. Push rods 19, 20 extend through bushings 33 in housing 36 and drive sapphire plungers 38, 40 in cylindrical heads 42, 44. Air vent holes 47 are provided in housing 36. Sapphire plungers 38, 40 are connected to push rods 19, 20 via holders 48 to which the plungers are bonded.

Holders 48 are flexibly attached in recesses 49 to push rods 19, 20. Springs 52 biased between washers 54, 56 provide the axial connection. Rounded end 58 pressing against bearing plate 60, in conjunction with a loose fit through hole 62, provides relative angular movement between each plunger and push rod. A loose fit between washer 56 and recess 49 allows relative radial motion between the parts.

Plungers 38, 40 extend through bushings 64 in mounting plates 66 and through seals 68 in heads 42, 44. Seals 68 are self-lubricating and constructed of fiber reinforced poly (tetrafluoroethylene). A spring member fits inside an annular recess (not shown) in each seal to provide radially-inward sealing pressure on each plunger. Vent holes 67 in mounting plates 66 provide an escape path for solvent leaking through seal 68.

Bores 70, 72 in heads 42, 44 receive plungers 38, 40 loosely, being about 6 mils greater in internal diameter than the plunger diameter. (The looseness of fit is exaggerated in FIG. 2.) Fluid enters bore 72 or primary head 44 through fitting 74, check valve 73, and forward radial passage 75. Fluid leaves the primary head into intermediate line 82 through rear radial passage 78, check valve 80, and fitting 81.

Line 82 is connected (FIG. 1) through holes (not shown) in housing 36 to pulse dampener 84 mounted in lower cavity 86 in the housing. As shown in FIG. 3, the pulse dampener consists of a coil of flattened tubing 88 supported in annular space 90 formed between two cylinders 92, 94. Line 96 connects the dampener output to bore 70 in accumulator head 42 via inlet fitting 98 and forward passage 104. Fluid leaves bore 70 into output line 110 through rear passage 106 and fitting 108. Output line 110 is connected to pressure transducer 112.

The transducer uses a flow-through Bourdon tube that intercepts a light beam to detect changes in pressure. Flow mixing is avoided by the flow-through construction. Outlet 114 of transducer 112 forms the pump output and is typically connected to a chromatography system.

Electronic circuitry (not shown) for controlling stepping motor 12 (to deliver a selected flow rate) and the pressure tranducer are described in Hutchins U.S. Pat. No. 3,855,515 and Abrahams et al. U.S. Pat. No. 3,855,129, both hereby incorporated by reference.

OPERATION

To operate the pump, a thumb dial on the face of the electronics assembly (not shown) mounted adjacent housing 36 is used to select flow rates from 0.1 to 9.9 ml/min in 0.1 ml/min increments, a pressure limit dial is set to between zero and 4500 psi, and the motor drive is switched on. If output pressure measured at transducer 112 exceeds the selected limit, the pump shuts down. The circuitry also uses the sensed pressure to compensate for the small reduction in volume caused by compression of the solvent.

As motor 12 turns shaft 18 and gear 24, push rods 19, 20 and plungers 38, 40 reciprocate 180° out of phase in relation to each other. The difference in radial offset of journals 30, 32 causes primary plunger 40 to travel through twice the distance travelled by the accumulator plunger 38 and thus to displace twice the solvent.

As primary plunger 40 advances, accumulator plunger 38 retracts. About 0.10 ml of solvent is forced out of open check valve 80 and delivered through lines 82, 96 and pulse dampener 84 to accumulator head 42. Half (about 0.05 ml) of the volume delivered is taken up within bore 70 as plunger 38 retracts half the distance travelled by plunger 40. The other half of the solvent (about 0.05 ml) exits through fitting 108 into line 110. Check valve 74 is closed and blocks outward flow into the input line.

In the other half of the cycle, plunger 38 advances and delivers 0.05 ml into output line 110. Check valve 80 is closed preventing any back flow into the primary head. Simultaneously, primary plunger 40 is retracting and filling bore 72 with fluid entering through open check valve 73.

Pulse dampener 84 acts as a solvent storage device, absorbing solvent when the flow rate (and pressure) is high and releasing solvent when the flow rate is low. Thus, as plunger 40 reaches the end of the retract cycle and the flow rate out of the primary head is approaching zero, dampener 84 supplies additional solvent to smooth the flow delivery during the shift between primary and accumulator heads. A similar smoothing is accomplished at the other shift, when the accumulator head stops advancing. Fluid storage is achieved by the expansion in cross section of flattened tube 88 as pressure rises. This provides storage without mixing of serial flow segments such as would occur in a reservoir-type storage device, thereby allowing rapid solvent changes.

In both heads 42, 44, outlet passages 78, 106 are spaced axially from the corresponding inlet passages 75, 104 to minimize mixing of upstream and downstream flow segments. The placement assures a full flush of the bores on each stroke and causes fluid first entering the head to also exit first. If gas bubbles enter the pump, they do not become trapped in either head. Check valve 80 will open to release the bubble from primary head 44 as soon as the solvent pressure drops. The absence of check valves on the accumulator head assures no bubble entrapment there.

Flattened tubing 88 is made from ¼ inch I.D. tubing with a 20 mil wall. Lines 82, 96 are integral portions of tubing 88, reduced in size to each have a 20 mil I.D. The interior cross section of tubing 88 measures about 300 mils by 2 to 5 mils under no pressure. In operation, the tubing expands to about 10 mils by 300 mils at high pressures. This is within the elastic limit of the tube walls, and thus the tube contracts back to its initial cross section when pressure is relieved. The tubing is constrained from expanding beyond about 10 mils by cylinders 92, 94, which form annulus 90. Above 10 mils, the tubing walls press against the cylinders, preventing further expansion.

OTHER EMBODIMENTS

Other embodiments of the invention will occur to those skilled in the art. For example, noncircular gears could be used to produce a more uniform flow; two motors, synchronized by a computer or other electronic device, could be used to drive the two plungers; the relative size and stroke of the primary and accumulator plungers could be varied; other one-way valves could substitute for ball-seat check valves 73, 80; pulse dampener 84 could be placed in line 110 between accumulator head 42 and transducer 112; and bores 70, 72 could be in a single head.

What is claimed is:

1. A fluid storage device for smoothing fluid delivery, said device comprising
    a length of flattened tubing,
        said tubing having first and second opposed wall portions adapted to bow outward when internal pressure increases, to thereby increase the internal volume per unit length of said tubing,
        said tubing defining an unobstructed flow passage therein,
    a first restraining wall positioned adjacent said first tube wall portion,
    a second restraining wall positioned adjacent said second tube wall portion,
        said second restraining wall being spaced from said first restraining wall such that said first and second tube wall portions are prevented from expanding beyond their elastic strain limits,
    whereby an increase in the pressure of fluid inside said tubing allows said walls to expand until they are restrained by said restraining means, and a decrease in said pressure allows said tubing to relax back to its original shape, thereby keeping the internal volume of said tubing small to reduce mixing between serial flow segments entering said fluid storage device.

2. A fluid storage device for smoothing fluid delivery, said device comprising
    a length of flattened tubing coiled in a helix,
        said tubing having generally flat, radially inward and outward wall portions adapted to bow radially inward and outward, respectively, when internal pressure increases, to thereby increase the internal volume per unit length of said tubing,
    an inner cylindrical restraining wall positioned adjacent to said radially inward wall portion, and
    an outer cylindrical restraining wall positioned adjacent to said radially outward wall portion,
        the radial separation between said walls being selected relative to the outside thickness of said tubing to restrain radially inward and outward bowing of said wall portions beyond their elastic strain limits,
    whereby an increase in the pressure of fluid inside said tubing allows said walls to expand until they are restrained by said restraining walls, and a decrease in said pressure allows said tubing to relax back to its original shape, thereby keeping the internal volume of said tubing small to reduce mixing between serial flow segments entering said fluid storage device.

* * * * *